United States Patent [19]

Blume et al.

[11] Patent Number: 4,925,481
[45] Date of Patent: May 15, 1990

[54] SUBSTITUTED BICYCLIC TRIAZOLE HERBICIDES

[75] Inventors: Friedhelm Blume; Gabriele Dorfmeister; Wilfried Franke; Richard Rees; Gerhard Johann; Friedrich Arndt, all of Berlin, Fed. Rep. of Germany

[73] Assignee: Schering Aktiengesellschaft, Fed. Rep. of Germany

[21] Appl. No.: 276,611

[22] Filed: Nov. 28, 1988

[30] Foreign Application Priority Data

Nov. 27, 1987 [DE] Fed. Rep. of Germany ....... 3740837

[51] Int. Cl.$^5$ .................... A01N 43/90; C07D 471/04
[52] U.S. Cl. ........................................ 71/92; 540/578; 544/127; 544/132; 546/119; 546/199; 548/262.4
[58] Field of Search ................ 546/119, 199; 540/578; 548/265; 544/127, 132; 71/92

[56] References Cited

U.S. PATENT DOCUMENTS 4,213,773  7/1980  Wolf .................................... 546/119

Primary Examiner—Mary G. Lee
Assistant Examiner—Bernard I. Dentz
Attorney, Agent, or Firm—Ostrolenk, Faber, Gerb & Soffen

[57] ABSTRACT

The invention relates to new heterocyclic substituted bicyclic triazoles of general formula I

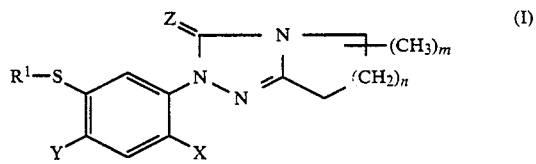

in which X, Y, Z, $R^1$, n and m have the meanings given in the description, processes for their preparation and their use as herbicides.

18 Claims, No Drawings

SUBSTITUTED BICYCLIC TRIAZOLE HERBICIDES

DESCRIPTION

This invention relates to new substituted bicyclic triazoles, processes for their preparation and their use as herbicides.

It is known that certain bicyclic triazoles possess herbicidal activity (DE-OS 28 01 429). However with these known selectivity problems can occur in important crops.

It has now been found that substituted bicyclic triazoles of general formula I

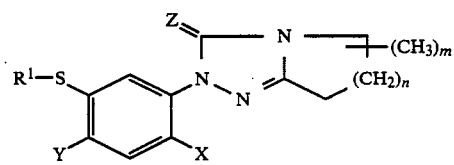

in which
X is hydrogen or fluorine,
Y is halogen,
Z is oxygen or sulphur,
$R^1$ is $C_1$-$C_6$-alkyl, $C_2$-$C_6$-alkenyl or $C_3$-$C_6$-alkynyl, each of which is optionally substituted by one or more halogen and/or $C_1$-$C_4$-alkoxy groups; $C_3$-$C_7$-cycloalkyl, $C_5$-$C_7$-cycloalkenyl, $C_3$-$C_7$-cycloalkyl-$C_1$-$C_3$-alkyl or $C_5$-$C_7$-cycloalkenyl-$C_1$-$C_3$-alkyl, each of which is optionally substituted by one or more halogen and/or $C_1$-$C_4$-alkoxy groups, and in which one or two carbons are optionally replaced by oxygen; cyano-$C_1$-$C_3$-alkyl or the group $CR^2R^3A$,
$R^2$ and $R^3$ are the same or different hydrogen, fluorine or methyl,
A is the group $CO_2R^4$, $COSR^5$ or $CONR^6R^7$,
$R^4$ is $C_1$-$C_6$-alkyl, $C_2$-$C_6$-alkenyl or $C_3$-$C_6$-alkynyl, each of which is optionally substituted by one or more halogen and/or $C_1$-$C_4$-alkoxy groups; $C_3$-$C_7$-cycloalkyl, $C_5$-$C_7$-cycloalkenyl, $C_3$-$C_7$-cycloalkyl-$C_1$-$C_3$-alkyl or $C_5$-$C_7$-cycloalkenyl-$C_1$-$C_3$-alkyl, each of which is optionally substituted by one or more halogen and/or $C_1$-$C_4$-alkoxy groups, and in which one or two carbons are optionally replaced by oxygen; or cyano-$C_1$-$C_3$-alkyl,
$R^5$ is $C_1$-$C_6$-alkyl, $C_2$-$C_6$-alkenyl or $C_3$-$C_6$-alkynyl, each of which is optionally substituted by one or more halogen and/or $C_1$-$C_4$-alkoxy groups,
$R^6$ and $R^7$ are the same or different hydrogen, $C_1$-$C_6$-alkyl, $C_2$-$C_6$-alkenyl or $C_3$-$C_6$-alkynyl, or together with the nitrogen to which they are attached are morpholino, piperidino or pyrrolidino,
n is 1, 2 or 3, and
m is 0, 1, 2 or 3,
show a very good selectivity to crops whilst at the same time have interesting herbicidal activity.

The expression "halogen" means fluorine, chlorine, bromine and iodine.

The compounds of the invention of general formula I can be prepared by a process in which (A) when Z is oxygen, a compound of general formula II

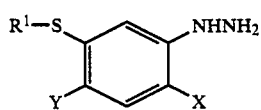

in which X, Y and $R_1$ have the meanings given under general formula I, is treated with a compound of general formula III

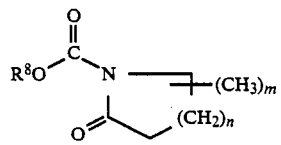

in which n and m have the meanings given under general formula I and $R^8$ is $C_1$-$C_4$-alkyl, in an inert solvent, in the presence of phosphorus pentoxide, or (B) a compound of general formula IV

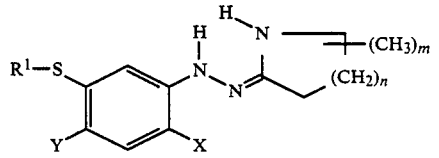

in which X, Y, $R^1$, n and m have the meanings given under general formula I, is treated, optionally as the salt, with a compound of general formula V

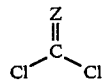

in which Z has the meaning given under general formula I and $R^8$ is $C_1$-$C_4$-alkyl, in an inert solvent, in the presence of a base.

The starting materials are known or can be prepared in an analogous method to known processes.

The process variant (A) is suitably carried out by reacting together, the starting materials of general formula II or III in a suitable solvent, at a temperature between 20° C. to 150° C., preferably at the boiling point of the solvent. Suitable solvents are for example halogenated hydrocarbons, such as for example methylene chloride or chloroform, or aromatic hydrocarbons, such as for example benzene, toluene, xylene, chlorobenzene or dichlorobenzene. The reaction time is from 0.5 to 15 hours.

The process variant (B) is suitably carried out by reacting the amidrazone of general formula IV or its salt with an acid (for example the hydrochloride) either with phosgene (Z=O) or thiophosgene (Z=S), in a suitable solvent, at a temperature range of 0° C. to 150° C., preferably at the boiling point of the solvent. Suitable solvents are for example halogenated hydrocarbons, such as for example methylene chloride or chloroform, ethers, such as for example tetrahydrofuran or dioxane, or aromatic hydrocarbons, such as for example benzene, toluene, xylene, chlorobenzene or dichlorobenzene. In order to neutralise acid formed during the reaction, a suitable base, preferably an amine, such as for example pyridine or triethylamine is used. The reaction time is from 1 to 24 hours.

The working up of the compounds of the invention prepared by the process variant (A) and (B) is carried out in conventional manner. Purification can be achieved by recrystallisation or column chromatography as well as by fractional distillation.

The compounds of the invention are generally colourless or slightly yellow crystalline or viscous substances, that are usually highly soluble in ethers, such as for example tetrahydrofuran, alcohols, such as for example methanol or ethanol, halogenated hydrocarbons, such as chloroform, sulphoxides, such as dimethyl sulphoxide, or esters, such as ethyl acetate.

The active substances of the invention show a good herbicidal activity against broad leaved weeds and grasses. A selective use of the compounds of the invention in various crops is possible for example in rape, beet, soya beans, cotton, rice, barley, wheat and other cereals. Individual active substances are particularly suitable as selective herbicides in beet, cotton, soya and cereals. However the compounds can be used for control of weeds in permanent crops, such as for example forestry, ornamental trees, fruit, vine, citrus, nut, banana, coffee, tea, rubber, oil palm, cocoa, berry fruit and hop plantations and for the selective control of weeds in annual crops.

The compounds of the invention can used for example against the following plant species:

Dioctyledonous weeds of the species Sinapis, Lepidium, Galium, Stellaria, Matricaria, Anthemis, Galinsoga, Chenopodium, Brassica, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Lamium, Veronica, Abutilon, Datura, Viola, Galeopsis, Papaver, Centaurea and Chrysanthemum.

Monocotyledonous weeds of the species Avena, Alopecurus, Echinochloa, Setaria, Panicum, Digitaria, Poa, Eleusine, Brachiaria, Lolium, Bromus, Cyperus, Agropyron, Sagittaria, Monocharia, Fimbristylis, Eleocharis, Ischaemum and Apera.

The rates of use vary depending on the manner of pre- and postemergent use between 0.03 and 5 kg/ha.

The compounds of the invention can also be used as defoliants, dessicants and total herbicides.

The compounds of the invention can be used either alone or in admixture with one another or with other active agents. Optionally, other plant-protective agents or pesticides can be added, depending on the purpose for the treatment. When it is desired to broaden the spectrum of activity, other herbicides can also be added. Herbicidally active mixing partners suitable in this connection include for example, the active agents listed in Weed Abstracts, vol. 34, No. 5 (1986) under the heading "Lists of common names and abbreviations employed for currently used herbicides and plant growth regulators in Weed Abstracts".

An improvement in the intensity and speed of action can be obtained, for example, by addition of suitable adjuvants, such as organic solvents, wetting agents and oils. Such additives may allow a decrease in the dose.

The designated active ingredients or their mixtures can suitably be used, for example, as powders, dusts, granules, solutions, emulsions or suspensions, with the addition of liquid and/or solid carriers and/or diluents and, optionally, binding, wetting, emulsifying and/or dispersing adjuvants.

Suitable liquid carriers are, for example aliphatic and aromatic hydrocarbons, such as benzene, toluene, xylene, cyclohexanone, isophorone, dimethyl sulphoxide, dimethylformamide and other mineral-oil fractions and plant oils.

Suitable solid carriers include mineral earths, e.g. bentonite, silica gel, talcum, kaolin, attapulgite, limestone, silicic acid and plant products, e.g. flours.

As surface-active agents there can be used for example calcium lignosulphonate, polyoxyethylenealkylphenyl ethers, naphthalenesulphonic acids and their salts, phenolsulphonic acids and their salts, formaldehyde condensates, fatty alcohol sulphates, as well as substituted benzenesulphonic acids and their salts.

The percentage of the active ingredient(s) in the various preparations can vary within wide limits. For example, the compositions can contain about 10 to 90 percent by weight active ingredients, and about 90 to 10 percent by weight liquid or solid carriers, as well as, optionally up to 20 percent by weight of surfactant.

The agents can be applied in customary fashion, for example with water as the carrier in spray mixture volumes of approximately 100 to 1,000 l/ha. The agents can be applied using low-volume or ultra-low-volume techniques or in the form of so-called microgranules.

The preparation of these formulations can be carried out in known manner, for example by milling or mixing processes. Optionally, individual components can be mixed just before use for example by the so-called commonly used tank-mixing method.

Formulations can be prepared, for example, from the following ingredients.

| (A) Wettable Powder | |
|---|---|
| (1) | 20 percent by weight active ingredient |
| | 68 percent by weight kaolin |
| | 10 percent by weight calcium lignosulphonate |
| | 2 percent by weight dialkylnaphthalenesulphonate |
| (2) | 40 percent by weight active ingredient |
| | 25 percent by weight kaolin |
| | 25 percent by weight colloidal silicic acid |
| | 8 percent by weight calcium lignosulphonate |
| | 2 percent by weight sodium salt of N-methyl-N-oleyltaurine |
| (B) Paste | |
| | 45 percent by weight active ingredient |
| | 5 percent by weight sodium aluminium silicate |
| | 15 percent by weight cetyl polyglycol ether with 8 mol of ethylene oxide |
| | 2 percent by weight spindle oil |
| | 10 percent by weight polyethylene glycol |
| | 23 percent by weight water |
| (C) Emulsifiable Concentrate | |
| | 20 percent by weight active ingredient |
| | 75 percent by weight isophorone |
| | 2 percent by weight ethoxylated castor oil |
| | 5 percent by weight calcium dodecylbenzenesulphonate |

The following examples illustrate the preparation of compounds according to the invention.

EXAMPLE 1

2-(4-Chloro-5-ethoxycarbonylmethylthio-2-fluorophenyl)-5,6,7,8-tetrahydro-1,2,4-triazolo[4,3-a]pyridin-3(2H)-one A solution of 4.2 g 4-chloro-5-ethoxycarbonylmethylthio-2-fluorophenylhydrazine and 2.6 g N-ethoxycarbonyl-2-piperidine in 50 ml xylene was treated with 1.1 g phosphorus pentoxide and the mixture heated under reflux for 3 hours. The solution was treated with water and extracted with ethyl acetate. The organic phase was dried over magnesium sulphate, concentrated and the residue purified by column chromatography (silica gel, eluent: hexane/ethyl acetate).

Yield: 1.2 g=21% of theory.

$n_D^{30}$: 1.5707.

In a similar manner to this example, the following compounds of the invention were prepared:

| Example No | R¹ | X | Y | Z | n | m | Physical Constant |
|---|---|---|---|---|---|---|---|
| 2 | —(CH₂)₂CN | F | Cl | O | 2 | 0 | mp.: 93° C. |
| 3 | —(CH₂)₂Cl | F | Cl | O | 2 | 0 | mp.: 88° C. |
| 4 | —CH(CH₃)₂ | F | Cl | O | 2 | 0 | mp.: 123° C. |
| 5 | —(CH₂)₄CH₃ | F | Cl | O | 2 | 0 | $n_D^{20}$: 1,57390 |
| 6 | —CH₂—CH=CH₂ | F | Cl | O | 2 | 0 | p.: 59° C. |
| 7 | —CH₂-(tetrahydrofuryl) | F | Cl | O | 2 | 0 | $n_D^{20}$: 1,58262 |
| 8 | (cyclopentyl) | F | Cl | O | 2 | 0 | mp.: 114° C. |
| 9 | —CH₂C≡CH | F | Cl | O | 2 | 0 | mp.: 102° C. |
| 10 | —CH₃ | F | Cl | O | 2 | 0 | mp.: 129° C. |
| 11 | —CH₂CO₂CH₃ | F | Cl | O | 2 | 0 | mp.: 80° C. |
| 12 | —CH₂CO₂CH(CH₃)₂ | F | Cl | O | 2 | 0 | mp.: 76° C. |
| 13 | —CH₂CO₂CH₂C≡CH | F | Cl | O | 2 | 0 | mp.: 81–83° C. |
| 14 | —CH₂CO₂C₅H₁₁ | F | Cl | O | 2 | 0 | $n_D^{20}$: 1,5571 |
| 15 | —CH₂CO₂-(cyclopentyl) | F | Cl | O | 2 | 0 | $n_D^{20}$: 1,5594 |
| 16 | —CHF₂ | F | Cl | O | 2 | 0 | mp.: 118° C. |

The following examples illustrate the possibilities for use of the compounds of the invention.

EXAMPLE A

In a greenhouse, the noted plant species were treated post-emegently with the noted compounds, at a rate of 0.1 kg active ingredient/ha. The compounds were sprayed evenly over the plants as emulsions or suspensions in 500 liters water/ha. Three weeks after the treatment, the compounds of the invention showed a high crop selectivity with excellent activity against the weeds. The comparison material did not show the high efficacy.

In the following table:
0 = no damage
4 = total destruction
TRZAX = *Triticum aestivum*
ZEAMX = *Zea mays*
HELAN = *Helianthus annuus*
SORHA = *Sorghum halepense*
ABUTH = *Abutilon theophrasti*
GALAP = *Galium aparine*
IPOSS = *Ipomoea purpurea*
MATCH = *Matricaria chamomilla*
POLSS = *Polygonum sp.*
SEBEX = *Sesbania exaltata*
SOLSS = *Solanum sp.*
VERPE = *Veronica persica*
VIOSS = *Viola sp*

| Compounds of invention | TRZAX | ZEMX | HELAN | SORHA | ABUTH | GALAP | IPOSS | MATCH | POLSS | SEBEX | SOLSS | VERPE | VIOSS |
|---|---|---|---|---|---|---|---|---|---|---|---|---|---|
| Example 1 | 0 | 0 | 4 | 3 | 4 | 4 | 4 | 3 | 4 | 4 | 4 | 4 | 4 |
| Example 2 | 2 | 1 | 3 | 3 | 4 | 3 | 4 | 2 | 1 | 3 | 4 | 4 | 2 |
| Example 6 | 2 | 1 | 2 | 3 | 4 | 4 | 3 | 3 | 3 | 4 | 4 | 4 | 3 |
| Example 7 | 1 | 1 | 2 | 2 | 1 | 3 | 1 | 3 | 3 | 4 | 4 | 4 | 3 |
| Example 11 | 1 | 1 | 4 | 2 | 4 | 3 | 4 | 3 | 3 | 4 | 4 | 4 | 4 |
| Example 12 | 0 | 2 | 4 | 1 | 4 | 2 | 4 | 3 | 2 | 3 | 4 | 3 | 2 |
| Example 13 | 0 | 0 | 4 | 1 | 4 | 2 | 4 | 2 | 2 | 4 | 4 | 4 | 3 |
| Example 14 | 1 | 1 | 4 | 1 | 4 | 3 | 4 | 3 | 2 | 4 | 4 | 3 | 3 |
| Example 15 | 1 | 0 | 4 | 2 | 4 | 3 | 4 | 3 | 3 | 3 | 4 | 4 | 3 |
| Untreated | 0 | 0 | 0 | 0 | 0 | 0 | 0 | 0 | 0 | 0 | 0 | 0 | 0 |
| Comparison Oxadiazon | 0 | 1 | 1 | 2 | 4 | 2 | 3 | 2 | 3 | 2 | 3 | 3 | 4 |

EXAMPLE B

In a greenhouse, the noted plant species were treated pre-emergently with the noted compounds, at a rate of 0.1 kg active ingredient/ha. The compounds were sprayed evenly over the plants as emulsions or suspensions in b 500 liters water/ha. Three weeks after the treatment, the compounds of the invention showed a high crop selectivity in soya (*Glycine max*/GLXMA), wheat (*Triticum aestivum*/TRZAX) and maize (*Zea mays*/ZEAMX) with excellent activity against the weeds. The comparison material did not show the similar high activity.

In the following table:
0 = no damage
4 = total destruction
GLXMA = *Glycine max*
TRZAX = *Triticum aestivum*
ZEAMX = *Zea mays*
ABUTH = *Abutilon theophrasti*
GALAP = *Galium aparine*
IPOSS = *Ipomoea purpurea*
MATCH = *Matricaria chamomilla*
SEBEX = *Sesbania exaltata*
SOLSS = *Solanum sp.*
VERPE = *Veronica persica*

| Compound of invention | GLXMAX | TRZAX | ZEAMX | ABUTH | GALAP | IPOSS | MATCH | SEBEX | SOLSS | VERPE |
|---|---|---|---|---|---|---|---|---|---|---|
| Example 1 | 0 | 0 | 0 | 4 | 3 | 4 | 4 | 4 | 4 | 3 |
| Untreated | 0 | 0 | 0 | 0 | 0 | 0 | 0 | 0 | 0 | 0 |
| Comparison Oxadiazon | 0 | 0 | 1 | 2 | 2 | 3 | 3 | 2 | 4 | 2 |

EXAMPLE C

In a greenhouse, the compounds noted in the table were applied at the rates mentioned. For this the active ingredients were added to vessels in 1500 ml water. Test plants that were treated were *Echinochloa crus-galli* (ECHCG), *Cyperus esculentus* (CYPES), *Cyperus difformis* (CYPDI) and *Sirpus juncoides* (SCPJU) in the 2 and 5 leaf stages. Three weeks after the application, the damage to the plants was assessed according to the following scheme:

0 = no damage
1 = slight damage
2 = medium damage
3 = serious damage
4 = total destruction
— = not tested

| Compound of the invention | Water application ppm | ECHCG | CYPES | CYPDI | SCPJU |
|---|---|---|---|---|---|
| Example 1 | 10 | 4 | 4 | 4 | 3 |
| Example 11 | 10 | 4 | — | — | — |
| Example 12 | 10 | 4 | — | — | — |
| Example 13 | 10 | 4 | — | — | — |
| Example 14 | 10 | 4 | — | — | — |

As the table shows the compounds of the invention have good activity against important rice weeds.

EXAMPLE D

In a greenhouse, the noted plant species were treated pre-emergently with the noted compounds, at a rate of 0.3 kg active ingredient/ha. The compounds were sprayed evenly over the plants as emulsions or suspensions in 500 liters water/ha. Three weeks after the treatment, the thio compound showed a high crop selectivity in maize (*Zea mays*/ZEAMX), with excellent activity against the weeds. The correspondin oxygen compound did not show the similar high activity.

In the following table:
0 = no damage
1 = 1-24% damage
2 = 25-74% damage
3 = 75-89% damage
4 = 90-100% damage In the following table:
0 = no damage
4 = total destruction
ZEAMX = *Zea mays*
SORHA = *Sorghum halepense*
ABUTH = *Abutilon theophrasti*
GALAP = *Galium aparine*
MATCH = *Matricaria chamomilla*
SOLSS = Solanum sp.
VERPE = *Veronica persica*

| Compounds of invention | ZEAMX | SORHA | ABUTH | GALAP | MATCH | SOLSS | VERPE |
|---|---|---|---|---|---|---|---|
| Example 1 | 0 | 3 | 4 | 4 | 4 | 4 | 3 |
| Comparison (DE-OS 2 801 429) 2-(4-Chloro-5-ethoxycarbonyl-methoxy-2-fluorophenyl)-5,6,7,8-tetrahydro-1,2,4-triazolo-[4,3-a]pyridin-3(2H)-one | 0 | 0 | 0 | 2 | 3 | 2 | 0 |

EXAMPLE E

In a greenhouse, the noted plant species were treated post-emergently with the noted compounds, at a rate of 0.03 kg active ingredient/ha. The compounds were sprayed evenly over the plants as emulsions or suspensions in 500 liters water/ha. Three weeks after the treatment, the thio compound showed a high crop selectively in maize (*Zea mays*/ZEAMX), with excellent activity against the weeds. The correspondin oxygen compound did not show the similar high activity.

In the following table:
0 = no damage
1 = 1-24% damage
2 = 25-74% damage
3 = 75-89% damage
4 = 90-100% damage In the following table:
0 = no damage
4 = total destruction
ZEAMX = *Zea mays*
ABUTH = *Abutilon theophrasti*
GALAP = *Galium aparine*
IPOSS = *Ipomoea purpurea*
MATCH = *Matricaria chamomilla*
SOLSS = Solanum sp.
VERPE = *Veronica persica*
VIOSS = Viola sp.

| Compounds of invention | ZEAMX | ABUTH | GALAP | IPOSS | MATCH | SOLSS | VERPE | VIOSS |
|---|---|---|---|---|---|---|---|---|
| Example 1 | 0 | 4 | 3 | 4 | 4 | 4 | 3 | 3 |
| Comparison (DE-OS 2 801 429) 2-(4-Chloro-5-ethoxycarbonyl-methoxy-2-fluorophenyl)-5,6,7,8-tetrahydro-1,2,4-triazolo-[4,3-a]pyridin-3(2H)-one | 0 | 0 | 0 | 0 | 0 | 0 | 0 | 0 |

We claim:
1. A substituted bicyclic triazole of the formula in which
X is hydrogen or fluorine,
Y is halogen,
Z is oxygen or sulphur,
$R^1$ is $C_1$-$C_6$-alkyl, $C_2$-$C_6$-alkenyl or $C_3$-$C_6$-alkynyl, each of which is optionally substituted by one or more halogen and/or $C_1$-$C_4$-alkoxy groups; $C_3$-$C_7$-cycloalkyl, $C_5$-$C_7$-cycloalkenyl, $C_3$-$C_7$-cycloalkyl-$C_1$-$C_3$-alkyl or $C_5$-$C_7$-cycloalkenyl-$C_1$-$C_3$-alkyl, each of which is optionally substituted by one or more halogen and/or $C_1$-$C_4$-alkoxy groups, and in which one or two carbons are optionally replaced by oxygen; cyano-$C_1$-$C_3$-alkyl or the group $CR^2R^3A$,
$R^2$ and $R^3$ are the same or different hydrogen, fluorine or methyl,
A is the group $CO_2R^4$, $COSR^5$ or $CONR^6R^7$, R⁴ is $C_1$–$C_6$-alkyl, $C_2$–$C_6$-alkenyl or $C_3$–$C_6$-alkynyl, each of which is optionally substituted by one or more halogen and/or $C_1$–$C_4$-alkoxy groups; $C_3$–$C_7$-cycloalkyl, $C_5$–$C_7$-cycloalkenyl, $C_3$–$C_7$-cycloalkyl-$C_1$–$C_3$-alkyl or $C_5$–$C_7$-cycloalkenyl-$C_1$–$C_3$-alkyl, each of which is optionally substituted by one or more halogen and/or $C_1$–$C_4$-alkoxy groups, and in which one or two carbons are optionally replaced by oxygen; or cyano-$C_1$–$C_3$-alkyl, R⁵ is $C_1$–$C_6$-alkyl, $C_2$–$C_6$-alkenyl or $C_3$–$C_6$-alkynyl, each of which is optionally substituted by one or more halogen and/or $C_1$–$C_4$-alkoxy groups, R⁶ and R⁷ are the same or different and are selected from the group consisting of hydrogen, $C_1$–$C_6$-alkyl, $C_2$–$C_6$-alkenyl or $C_3$–$C_6$-alkynyl, or together with the nitrogen to which they are attached are morpholino, piperidino or pyrrolidino, n is 1, 2 or 3, and m is 0, 1, 2 or 3.

2. A substituted bicyclic triazole according to claim 1 in which X is fluorine, Y is chlorine, Z is oxygen, n is 2 and m is 0.

3. A substituted bicyclic triazole according to claim 2 in which R¹ is $CH_2CO_2R^4$ and R⁴ is alkyl or alkynyl.

4. A substituted bicyclic triazole according to claim 3 in which R¹ is selected from the group consisting of —$CH_2CO_2CH_3$, —$CH_2CO_2CH(CH_3)_2$, —$CH_2CO_2CHC\!=\!CH$ and —$CH_2CO_2C_5H_{11}$.

5. A substituted bicylic triazole according to claim 2 in which R¹ is selected from the group consisting of

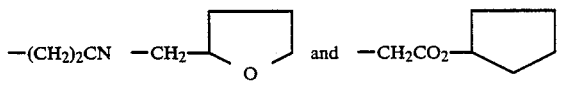

6. 2-(4-Chloro-5-ethoxycarbonylmethylthio-2-fluorophenyl)-5,6,7,8-tetrahydro-1,2,4-triazolo[4,3-a]pyridin-3(2H)-one according to claim 1.

7. A herbicidal composition which comprises an effective amount of a compound according to claim 1, in admixture with carriers and diluents.

8. A herbicidal composition which comprises an effective amount of a compound according to claim 2, in admixture with carriers and diluents.

9. A herbicidal composition which comprises an effective amount of a compound according to claim 3, in admixture with carriers and diluents.

10. A herbicidal composition which comprises an effective amount of a compound according to claim 4, in admixture with carriers and diluents.

11. A herbicidal composition which comprises an effective amount of a compound according to claim 5, in admixture with carriers and diluents.

12. A herbicidal composition which comprises an effective amount of a compound according to claim 6, in admixture with carriers and diluents.

13. A method of combating weeds which comprises applying to the weeds or their locus an effective amount of a compound according to claim 1.

14. A method of combatting weeds which comprises applying to the weeds or their locus an effective amount of a compound according to claim 2.

15. A method of combatting weeds which comprises applying to the weeds or their locus an effective amount of a compound according to claim 3.

16. A method of combatting weeds which comprises applying to the weeds or their locus an effective amount of a compound according to claim 4.

17. A method of combatting weeds which comprises applying to the weeds or their locus an effective amount of a compound according to claim 5.

18. A method of combatting weeds which comprises applying to the weeds or their locus an effective amount of a compound according to claim 6.

* * * * *